United States Patent
Burvall

(10) Patent No.: US 8,801,687 B2
(45) Date of Patent: Aug. 12, 2014

(54) ABSORBENT ARTICLE COMPRISING A STIFFENING ELEMENT AND A DEVICE FOR DISPOSAL

(75) Inventor: Angelica Burvall, Bollebygd (SE)

(73) Assignee: SCA Hygiene Products AB, Gothenburg (SE)

( * ) Notice: Subject to any disclaimer, the term of this patent is extended or adjusted under 35 U.S.C. 154(b) by 328 days.

(21) Appl. No.: 13/254,598

(22) PCT Filed: Mar. 6, 2009

(86) PCT No.: PCT/SE2009/050238
§ 371 (c)(1),
(2), (4) Date: Sep. 2, 2011

(87) PCT Pub. No.: WO2010/101501
PCT Pub. Date: Sep. 10, 2010

(65) Prior Publication Data
US 2012/0109096 A1    May 3, 2012

(51) Int. Cl.
*A61F 13/56* (2006.01)
(52) U.S. Cl.
CPC ..................................... *A61F 13/56* (2013.01)
USPC ................................ 604/385.31; 604/385.13
(58) Field of Classification Search
CPC ................... A61F 2013/8402; A61F 13/4702; A61F 13/47218; A61F 13/5515; A61F 13/5611; A61F 13/47272; A61F 2013/15357; A61F 13/56
USPC .................. 604/354, 385.01, 385.13, 385.16, 604/385.31, 385.201, 389, 390
See application file for complete search history.

(56) References Cited

U.S. PATENT DOCUMENTS

| | | | |
|---|---|---|---|
| 3,688,771 A | 9/1972 | Werner | |
| 6,451,000 B1 * | 9/2002 | Hayase et al. | 604/385.13 |
| 6,932,801 B1 | 8/2005 | Samuelsson | |
| 2003/0125699 A1 * | 7/2003 | Drevik et al. | 604/385.31 |
| 2003/0125701 A1 | 7/2003 | Widlund | |
| 2003/0153891 A1 | 8/2003 | Molee | |
| 2005/0090793 A1 | 4/2005 | Winqvist | |

FOREIGN PATENT DOCUMENTS

| | | |
|---|---|---|
| EP | 0 712 619 | 8/2002 |
| EP | 1 395 218 | 2/2006 |

(Continued)

OTHER PUBLICATIONS

Extended European search report dated May 27, 2013, issued in counterpart European Patent Application No. 09841225.7 (4 pages).

*Primary Examiner* — Tan-Uyen T Ho
*Assistant Examiner* — Peter S Vasat
(74) *Attorney, Agent, or Firm* — Drinker Biddle & Reath LLP

(57) ABSTRACT

An absorbent article including an absorption member including an absorbent body for absorbing body fluids. The absorption member having an upper side intended to face a wearer during use of the article and a lower side intended to face away from the wearer during use of the article, and a stiffening element that, at least during use of the article, provides the article with a predetermined shape that enhances the fit of the article to the wearer's body. The stiffening element is fastened to the lower side of the absorption member and the stiffening element includes a piece of material formed into a layered structure that significantly contributes to the stiffness of the stiffening element. The layered structure can be extended to a non-layered structure. The piece of material is provided with a first attachment for locking a rolled up or folded used article.

12 Claims, 5 Drawing Sheets

(56) References Cited

FOREIGN PATENT DOCUMENTS

| | | |
|---|---|---|
| JP | 2007-654 | 1/2007 |
| JP | 2007-215948 | 8/2007 |
| WO | 98/22061 | 5/1998 |
| WO | WO-99/00081 A1 | 1/1999 |
| WO | 01/17474 | 3/2001 |
| WO | 2006/130053 | 12/2006 |
| WO | 2006/130054 | 12/2006 |

* cited by examiner

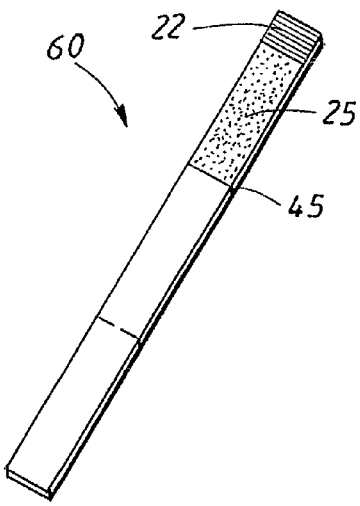
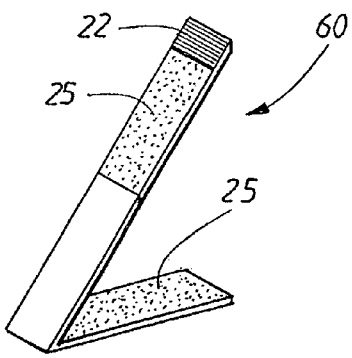
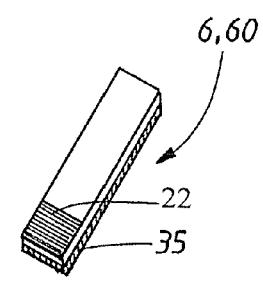
FIG.13a     FIG.13b     FIG.13c
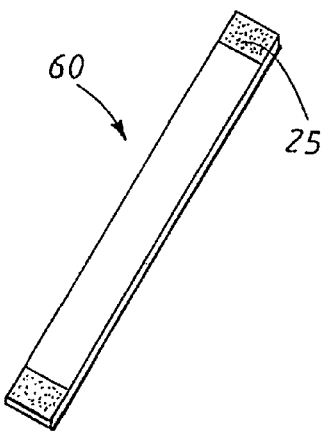
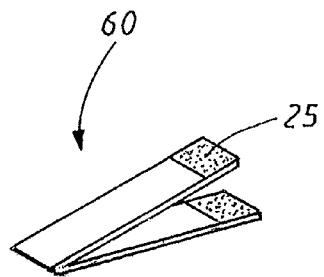
FIG.14a     FIG.14b
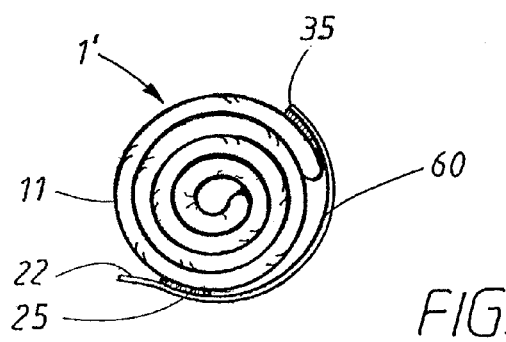
FIG.15

ABSORBENT ARTICLE COMPRISING A STIFFENING ELEMENT AND A DEVICE FOR DISPOSAL

CROSS-REFERENCE TO PRIOR APPLICATION

This application is a §371 National Stage Application of PCT International Application No. PCT/SE2009/050238 filed Mar. 6, 2009, which is incorporated herein in its entirety.

FIELD-OF THE INVENTION

The present disclosure relates to an absorbent article, such as a sanitary napkin, a panty liner or an incontinence protector, including an absorption member and a stiffening element that, at least during use of the article, provides the article with a certain, predetermined shape that enhances the fit of the article to the wearer's body.

BACKGROUND

Absorbent articles, such as sanitary napkins, incontinence guards, panty-liners, diapers etc., are known in the art. An important function of absorbent articles is to prevent leakage of body exudates during use of the article. Generally, the article should fit well to the user and stay in place during use. This also enhances the user comfort.

With regard to at least sanitary napkins, incontinence guards and panty-liners, it is previously known to provide the article with stiff or elastic shaping elements that provide the article with a shape that improves the fitting and the ability to stay in place during use. In general, a stiff shaping element has the advantage that the shape of the article is predetermined and maintained during use. On the other hand, stiff shaping elements should be designed with particular care in order not to cause discomfort during use of the article. It is also known to provide the underside of sanitary napkins and similar absorbent articles with fastening means, such as adhesives, for attachment to the user's garments.

WO 0117474 discloses an example of an absorbent article in the form of a sanitary napkin, a panty liner or an incontinence protector, wherein the rear portion of the article includes a longitudinally extending ridge-shaped elevation forming a stiff shaping element that partially extends between the wearer's buttocks during use of the article. This provides good protection against rearward leakage.

WO 98/22061 discloses an absorbent article in the form of a sanitary napkin having stiff front and crotch portions wherein the front portion is curved and inclined upwards, towards the user, with respect to the crotch portion. Further, the article has a narrow waist in the crotch portion allowing a high stiffness without causing discomfort. The desired stiffness is achieved by e.g. including a rigid shape-retaining, spoon-shaped, plastic or metal layer inside the article. The article according to WO 98/22061 is intended to be kept securely and comfortably in position against the body of the user during use, without the need for particular attachment means.

EP 1395218 discloses an adsorbent article in the form of a sanitary towel or incontinence pad including a combined, flat stiffening and absorbent element arranged inside the article, which element gives the article in different regions a predetermined two- or three-dimensional shape (including curvature, bowl-shape and a raised part between the buttocks of the wearer) during use of the article, i.e. when the article is affected by compressive forces generated by the thighs of the wearer. In similarity to WO 98/22061, the front and crotch portions are designed to allow anchoring of the article to thigh muscle tendons, which gives the article a good fit and stability in the fitted position.

Although the known absorbent articles with stiffening elements in many cases provide for a good fit, there still remains a need to further develop this type of absorbent articles.

SUMMARY

It is desired to provide a well-fitting absorbent article, such as a sanitary napkin, that exhibits improved properties compared to conventional absorbent articles with stiff shaping elements. This can be achieved by the disclosed article.

A first aspect relates to an absorbent article, such as a sanitary napkin, a panty liner or an incontinence protector. The article has a longitudinal direction and a transverse direction, a front portion, a rear portion, a crotch portion located between the front portion and the rear portion, and a peripheral edge. The article includes an absorption member including an absorbent body for absorbing body fluids. The absorption member has an upper side intended to face a wearer during use of the article and a lower side intended to face away from the wearer during use of the article, and a stiffening element that, at least during use of the article, provides the article with a predetermined shape that enhances the fit of the article to the wearer's body.

The stiffening element is fastened to the lower side of the absorption member, and the stiffening element includes a piece of material formed into a layered structure that significantly contributes to the stiffness of the stiffening element. The layered structure can be extended to a non-layered structure, and the piece of material can be provided with first attachment means for locking a rolled up or folded used article.

The term absorption member as used herein refers to an item that includes an absorption body for absorption of body fluids. The absorption member also includes, for example, a liquid permeable top-sheet arranged on the upper side of the absorption body and a liquid-impermeable back sheet arranged on the lower side of the absorption body.

The disclosed design has the advantage that the stiffening element provides the absorbent article with a good body fit as well as works as a disposable means. Thus, the stiffening element of the absorbent article, which alternatively may be denoted stiff shaping element, has a multifunction: i) shaping of the article during use and ii) locking a folded or rolled article after use. Conventionally, these functions are provided by separate items. Multifunction is useful for decreasing the number of components in the absorbent article which makes the manufacture more effective. In addition, less material is required.

Because the piece of material is formed into a layered structure it can significantly contribute to the stiffness of the stiffening element even if the material itself, i.e. when non-layered, is not particularly stiff. By allowing extension of the piece of material from this contracted or compressed, layered structure into an extended, non-layered structure, and by providing the piece of material with e.g. adhesives, it becomes possible to use the same piece of material for the two purposes.

In an advantageous embodiment, the layered structure is formed by folding the piece of material. Folding of a material makes it possible to build up a sufficient stiffness. Folding is also suitable with regard to manufacture. Further, a folded, layered structure can be extended by unfolding.

In a further advantageous embodiment, the piece of material includes second attachment means for detachably attaching the layers in the layered structure. Thereby, the shape of the layered structure can be safely maintained during use of the article. In a particular embodiment, a portion of the second attachment means forms the first attachment means. Thereby, no additional attachment means are required.

In a further advantageous embodiment, at least a part of the stiffening element has an elongated shape and extends in the longitudinal direction of the article. In particular embodiments, the part of the stiffening element extends over at least a part of the rear portion. In particular embodiments, the part of the stiffening element is arranged to form a ridge-shaped elevation on the upper side of the absorption member, which elevation partially extends between the wearer's buttocks during use of the article. Such a stiffening element is relatively easy to produce and fasten to the absorbent article, and it prevents rearward leakage. In particular embodiments, the part of the stiffening element includes a strip of material that has been folded such as to form the elongated shape. This allows for a simple and effective production.

In a further advantageous embodiment, the piece of material forming the layered structure is provided with a gripping flap arranged to allow extension of the layered structure when pulled. This simplifies the conversion of the stiffening element to a means for locking a rolled/folded article after use.

In a further advantageous embodiment, the stiffening element exhibits a stiffness that is higher than a part of the absorbent article that surrounds the stiffening element. For example, the stiffening element should be stiffer than the absorbent member. This has the effect that folding indications are provided along and/or around the stiffening element. These folding indications, together with e.g. the size and geometry of the stiffening element, determine which shape the article will acquire during use.

In a further advantageous embodiment, the absorbent member includes, at its upper side, a liquid-permeable top-sheet and, at its lower side, a liquid-impermeable back sheet, wherein the absorbent body is arranged between the sheets.

As used herein, a permanent fixation, bond or attachment is a fixation, bond or attachment that is intended to withstand normal use and wear and that cannot be broken without destroying or damaging at least one of the items involved in the fixation. An example of a fixation that can be permanent is the fastening of the piece of material forming the layered structure to the lower side of the absorption member. When the layered structure is extended to the non-layered structure the piece of material should not come loose from the absorption member. A releasable or detachable join is a bond or attachment that can be broken without damaging or destroying the items involved.

BRIEF DESCRIPTION OF THE DRAWINGS

In the description of embodiments of the invention given below reference is made to the following figures, in which:

FIGS. 13a-13c show a second example of how a piece of material can be formed into a layered structure and form a suitable stiffening element according to embodiments of the invention, FIGS. 14a-14b show a third example of how a piece of material can be formed into a layered structure and form a suitable stiffening element according to embodiments of the invention, and FIG. 15 shows an example of a used article that has been locked in a rolled up mode.

DETAILED DESCRIPTION OF PREFERRED EMBODIMENTS

Figure 1:
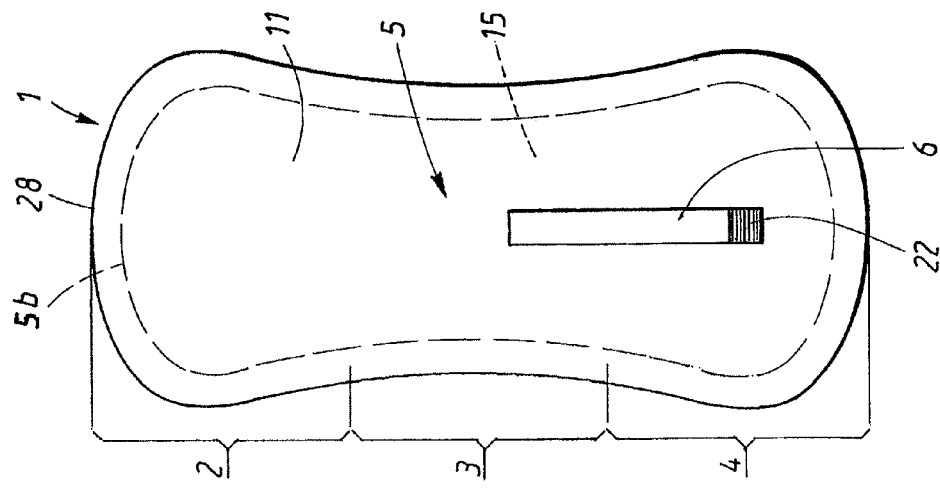
FIG. 1 shows, in a view from below, a first embodiment of the invention.

FIG. 1 shows, in a view from below, a first embodiment of an absorption article 1. The article 1 has a longitudinal direction and a transverse direction, a front portion 2, a rear portion 4, a crotch portion 3 located between the front portion 2 and the rear portion 4, and a peripheral edge 28. The division of the article 1 into these portions is not strict but describes, in a conventional way, the intended positioning of the article 1 in relation to a wearer.

The article 1 includes an absorption member 5 having an upper side 15 (facing downwards in FIG. 1) intended to face a wearer during use of the article 1 and a lower side 11 intended to face away from the wearer during use of the article 1. The absorption member 5 exemplified in the figures of this document is structured in a conventional way and includes a liquid-permeable top-sheet 5a, an absorbent body 5b for absorbing body fluids, and a liquid-impermeable back sheet 5c (see FIG. 10). The top-sheet 5a and the back sheet 5c are in a conventional way interconnected around an outer edge of the absorbent body 5b such as to form a cover around the absorbent body 5b. Thus, the liquid-impermeable back sheet 5c forms the lower side 11 of the absorption member 5. In FIG. 1, the absorbent body 5b is indicated with a dashed line.

Suitable materials and material combinations for forming the top-sheet 5a, the absorbent body 5b and the back sheet 5c are well known to the person skilled in the art. Examples of suitable materials are non-woven fabrics and perforated plastic films for the top-sheet 5a; cellulose fibers, absorbing foam material and super absorbents (SAP) for the absorbent body 5b; and polyethylene film and non-woven fabrics treated with hydrophobing agents for the back sheet 5c.

The article 1 further includes a stiffening element 6 fastened to the lower side 11 of the absorbent member 5, i.e. to the back sheet 5c. As will be further described below, the stiffening element 6 is stiffer than parts of the article 1 surrounding the stiffening element 6 and provides, at least during use, the article 1 with a certain, predetermined shape that enhances the fit of the article 1 to the wearer's body.

The stiffening element 6 includes a strip of material that has been folded into a layered structure and is provided with a gripping flap 22 to be used when unfolding the layered structure. The stiffening element 6 is secured to the absorbent member 5 at a point some layers below the gripping flap 22, i.e. a part of the layer that is positioned closest to the absorbent layer 5 is secured, e.g. by means of adhesives, to the absorbent member 5. When unfolded, the strip of material can be used to lock a rolled-up or folded article after use. The structure and disposal function of the stiffening element 6 is further described below.

In FIG. 1, the stiffening element 6 has an elongated shape and extends longitudinally in a central position in the rear portion 4 of the article 1. A stiffening element 6 arranged in this way forms a ridge-shaped elevation on the upper side 15 of the absorbent member 5, which elevation partially extends between the wearer's buttocks during use of the article. This prevents rearward leakage.

FIGS. 2-9 show further preferred embodiments of the inventive absorption article 1. As will be described below, the main difference between the different embodiments is the geometry and/or the positioning of the stiffening element. All stiffening elements shown in FIGS. 1-9 include a piece of material that has been folded such as to form a layered structure. Where also the absorption member differs from what is described in relation to FIG. 1, this is also described below.

Figure 2:
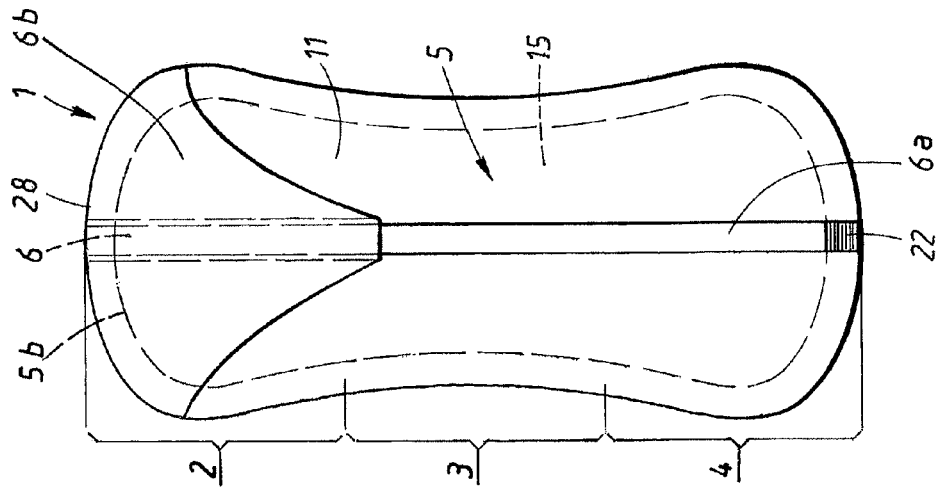
FIG. 2 shows, in a view from below, a second embodiment of the invention.

FIG. 2 shows, in a view from below, a second preferred embodiment of an inventive absorption article 1. In this case the stiffening element 6 extends primarily over the front portion 2 of the article 1. The layered structure comprises in this case two integrated parts. A folded, elongated, narrow part, similar to what is shown in FIG. 1, extends longitudinally in a central position in the front portion 2 of the article 1. Instead of ending with a gripping flap, as in FIG. 1, the narrow part transforms, at a position somewhat into the crotch portion 3, into a gradually widening part 6b that gradually widens symmetrically as it extends in a frontal direction of the article 1. This wider part 6b thus forms a layer in the layer structure that is located furthest away from the absorbent member 5. At a position in a front part of the front portion 2, the wider part 6b has widened to a width corresponding to the width of the absorption member 5. Roughly, the wider part 6b has the shape of a regular triangle with a tip pointing in a rear direction of the article, but where said tip is replaced by the narrow part of the layered structure which is folded below the wider part 6b. Further, the sides of this "triangle" are rounded such as to fit to the user and to the peripheral edge 28 of the article. In this embodiment, the layered structure includes layers of different widths, wherein the wider part 6b forms a layer that covers the narrow part. Also the wider part 6b may be folded such as to form a plurality of layers.

A part 6a of the piece of material forming the layered structure of the stiffening element 6 extends longitudinally over both the crotch and rear portions 3, 4. FIG. 2 thus shows an example of a part 6a of the piece of material forming the layered structure of the stiffening element 6 may extend outside the layered structure already before pulling the gripping flap 22. The non-layered material part 6a is detachably attached to the absorbent member 5 in both the crotch and rear portions 3, 4 to stay in place during use of the article 1. This detachable attachment can be achieved by distributing suitable fastening means, such as adhesives, over the length of the part 6a.

When pulling and lifting the gripping flap 22 in the embodiment shown in FIG. 2, the non-layered material part 6a comes loose from the absorbent member 5 and the layered structure, i.e. the narrow part of the stiffening element 6 together with the wider part 6b, unfolds. The stiffening element 6 is in this case secured to the absorbent member 5 via the wider part 6b along parts of the peripheral edge 28.

A stiffening element 6 arranged according to FIG. 2 allows anchoring of the article 1 to/between the thigh muscle tendons of the user and prevents the article from moving backwards during use. It also provides a ridge-shaped elevation on the upper side 15 of the absorbent member 5, which means that the stiffening element according to FIG. 2 alternatively can be arranged in the rear portion 4 such that the elevation partially extends between the wearer's buttocks during use of the article. In similarity with what is described in relation to FIG. 1, this prevents rearward leakage.

Figure 3:
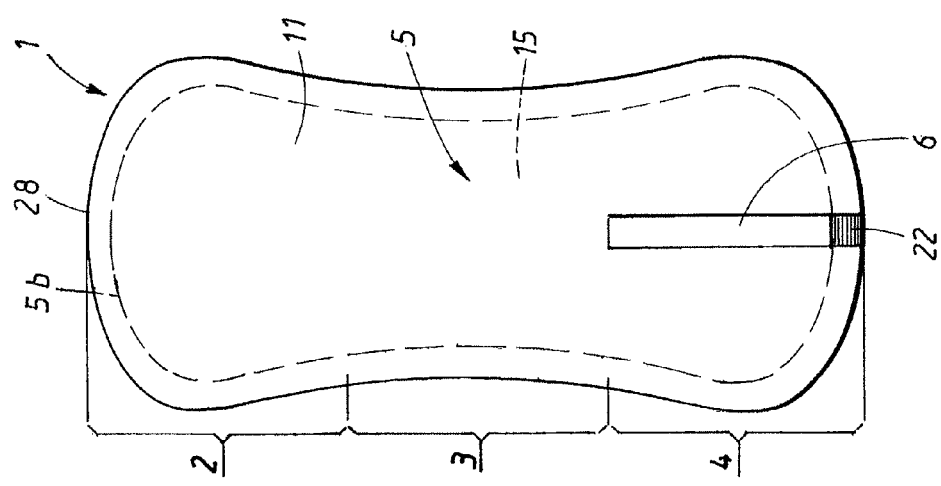
FIG. 3 shows, in a view from below, a third embodiment of the invention.

FIG. 3 shows, in a view from below, a third preferred embodiment of an inventive absorption article 1. In this case the stiffening element 6 is displaced, in relation to FIG. 1, towards the front portion 2, such as to extend somewhat into the crotch portion 3. The shape provided by the stiffening element 6 is similar to the shape described in relation to FIG. 1.

Figure 4:
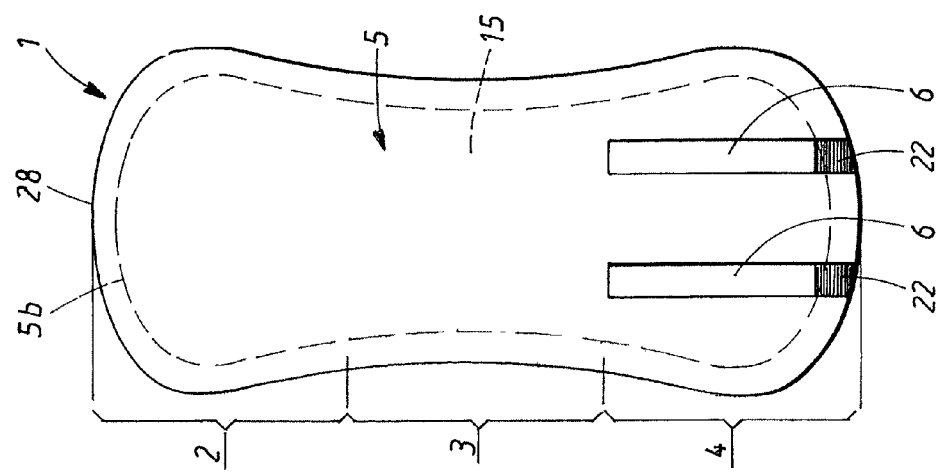
FIG. 4 shows, in a view from below, a fourth embodiment of the invention.

FIG. 4 shows, in a view from below, a fourth preferred embodiment of an inventive absorption article 1. In this case the article 1 includes two stiffening elements 6 extending in parallel in a longitudinal direction over most of the crotch portion 4. Also in this case a ridge-shaped elevation on the upper side 15 of the absorbent member 5, which elevation partially extends between the wearer's buttocks during use of the article, is formed. This is due to the fact that the stiffness of the stiffening elements 6 is higher than the stiffness of the absorption member 5. To achieve this effect, it is not necessary that the stiffening elements 6 are parallel. The stiffening elements 6 may point towards a longitudinal center line of the article 1 as seen in a direction towards the front portion 2 of the article 1. The gripping flaps 22 may be connected by a piece of material so that the user only needs to handle one combined gripping flap. The material used for such a connection should be flexible so that it does not influence the shape of the article 1.

Figure 5:
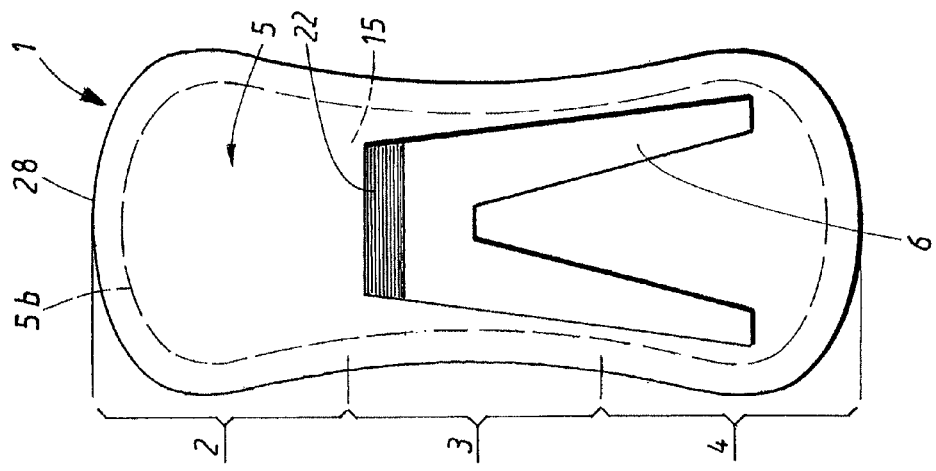
FIG. 5 shows, in a view from below, a fifth embodiment of the invention.

FIG. 5 shows, in a view from below, a fifth preferred embodiment of an inventive absorption article 1. In this case the stiffening element 6 has the shape of a pair of trousers having legs connected at a waist part that is placed in the crotch portion 3 and where the legs extend towards and into the rear portion 4. Each leg extends somewhat away from a longitudinal center line of the article 1. These legs have the same function as the two stiffening elements in the fourth embodiment. The length of the legs and the location of the waist part can be varied. An advantage compared to the embodiment shown in FIG. 4 is that the user only needs to handle one gripping flap 22.

Figure 6:
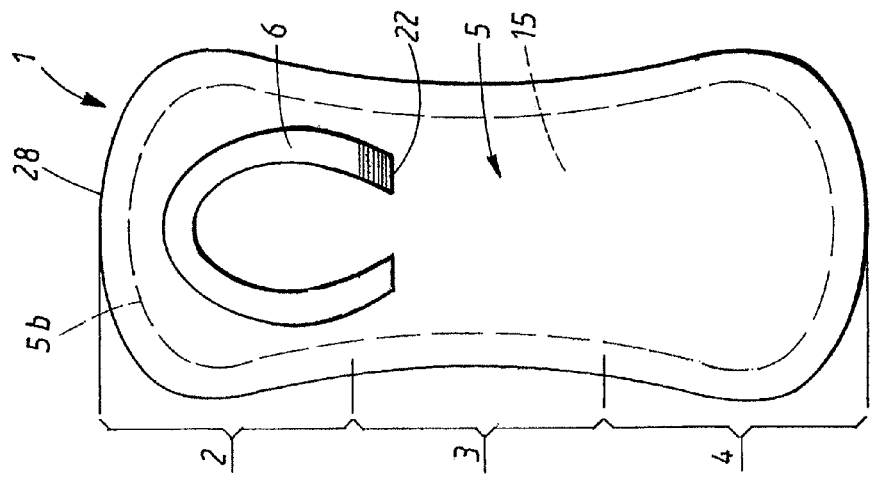
FIG. 6 shows, in a view from below, a sixth embodiment of the invention.

FIG. 6 shows, in a view from below, a sixth preferred embodiment of an inventive absorption article 1. In this case the stiffening element 6 is positioned in the front portion 2 and has the shape of a horseshoe with the open part directed towards the rear portion 4 of the article 1. Such a stiffening element 6 is useful for providing a bowl-shaped front portion 2 and for anchoring the article 1 to/between the thigh muscle tendons of the wearer. This enhances the body fit of the article 1 and reduces the risk of backward movement of the article 1 during use.

Figure 7:
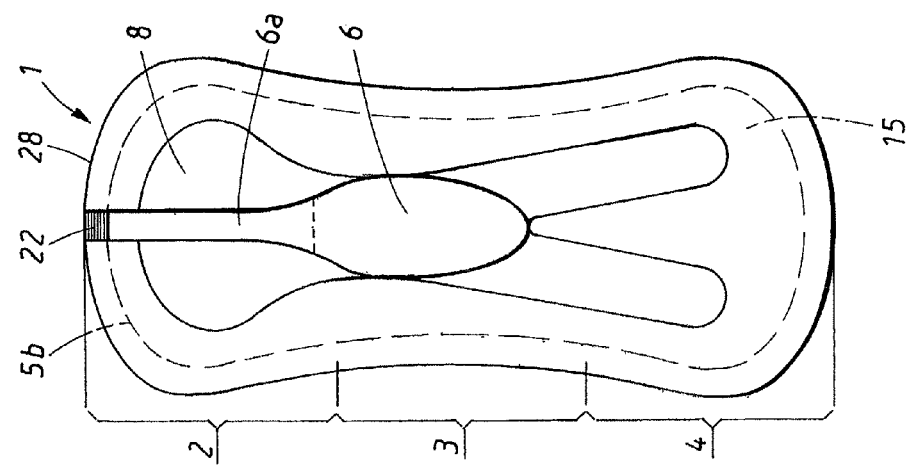
FIG. 7 shows, in a view from below, a seventh embodiment of the invention.

FIG. 7 shows, in a view from below, a seventh preferred embodiment of an inventive absorption article 1. In this case the stiffening element 6 is positioned in the crotch portion 3 and has an oval shape. A non-layered, unfolded part 6a of the piece of material making up the layered structure extends longitudinally over the front portion 2. The gripping flap 22 is positioned at the end of this unfolded part 6a. Thus, in the crotch portion 3 the piece of material forms a layered structure having an oval shape as seen in a lateral plane of the article 1. The stiffening element 6, i.e. the layered structure, is fastened to the absorbent member 5 by fastening the closest layer to the absorbent member 5. In this case the stiffening element 6 forms a ridge or "hump" that protrudes on the upper side 15 of the absorbent member 5.

In the example shown in FIG. 7, the inventive, outer stiffening element 6 is combined with a second, inner stiffening element 8 that is located inside the absorbent member 5. Such inner or integrated stiffening elements are known from e.g. EP 1395218. Various combinations of outer and inner stiffening elements are possible, e.g. various geometries can be combined in order to improve the fitting of the article.

Figure 8:
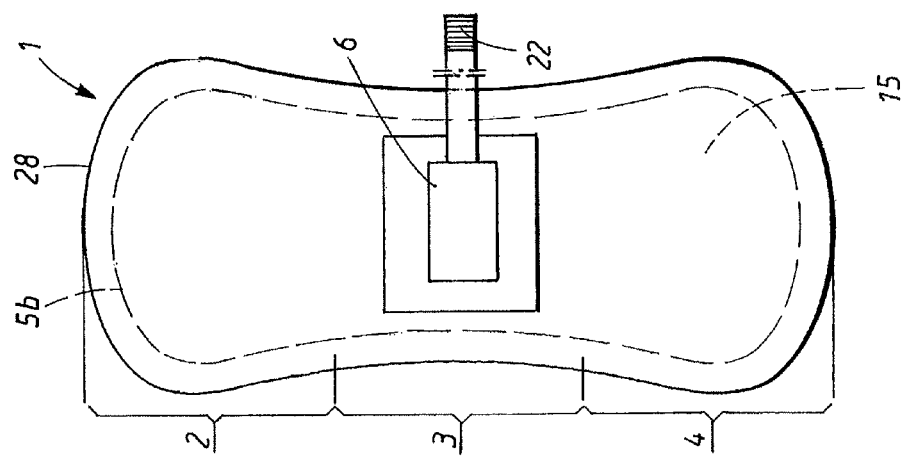
FIG. 8 shows, in a view from below, an eighth embodiment of the invention.

FIG. 8 shows, in a view from below, an eighth preferred embodiment of an inventive absorption article 1. In this case the layered structure making up the stiffening element 6 has been partly extended to a non-layered piece of material by pulling the gripping member 22 in a transversal direction of the article 1. The primary purpose of this figure is to show that the extension of the layered structure not necessarily needs to be directed in the longitudinal direction. The stiffening element 6 shown in FIG. 8 forms a hump in a similar way as described in relation to FIG. 7.

Figure 9:
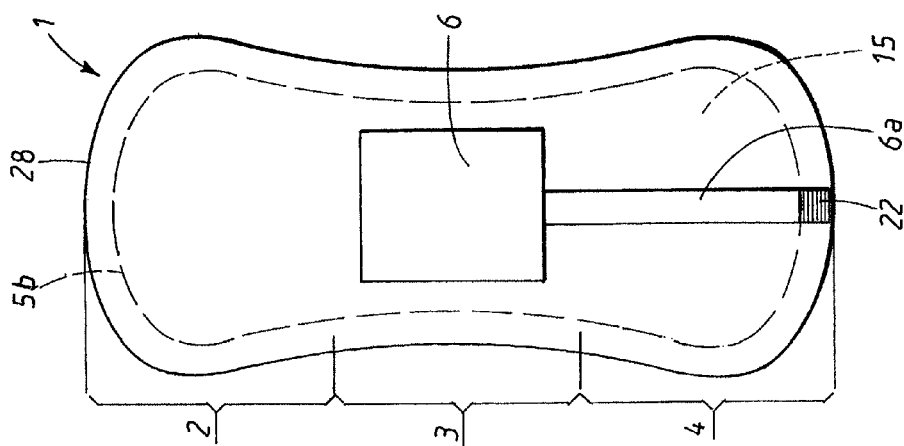
FIG. 9 shows, in a view from below, a ninth embodiment of the invention.

FIG. 9 shows, in a view from below, a ninth preferred embodiment of an inventive absorption article 1. Again it is shown an example of that a part 6a of the piece of material forming the layered structure of the stiffening element 6 may extend outside the layered structure already before pulling the gripping flap 22.

Various combinations of the embodiments shown in FIGS. 1-9 are possible. For instance, stiffening elements can be positioned both in the front portion 2 and in the rear portion 4. Further, the side of the stiffening element 6 facing away from the user may be provided with fastening means, such as hooks or adhesive, for attachment to the undergarments of the user.

Figure 10:
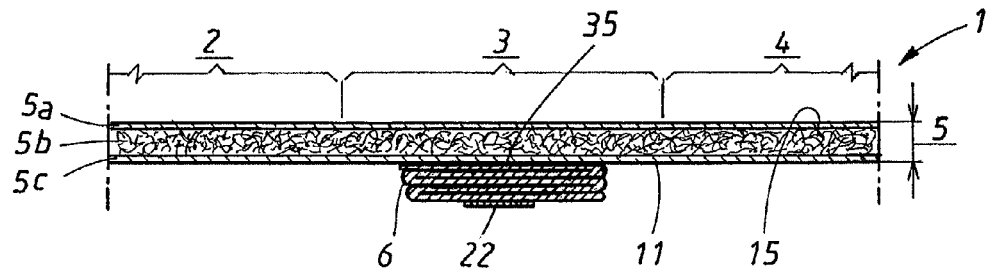
FIG. 10 shows, in a sectional side view, still another embodiment of the invention.

FIG. 10 shows a sectional side view of still another preferred embodiment of the inventive absorbent article 1. In FIG. 10 it can be seen that the absorption member 5 includes the top sheet 5a, the absorption body 5b and the back sheet 5c, wherein the top sheet 5a forms the upper side 15, and the back sheet 5c the lower side 11, of the absorption member 5. It can further be seen that the stiffening element 6 is arranged at the lower side 11 of the absorption member 5. FIG. 10 is cut at its ends, which for instance means that FIG. 10 does not show that the top-sheet 5a and the back sheet 5c are interconnected around the outer edge of the absorbent body 5b such as to form a cover around the absorbent body 5b. This is, however, shown in FIG. 11.

Figure 11:
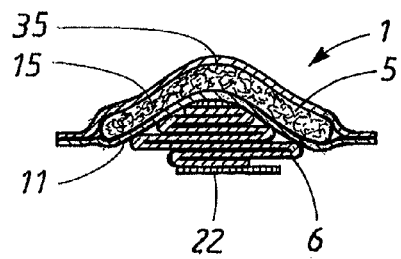
FIG. 11 shows the embodiment shown in FIG. 10, but this time in a sectional transversal view and during use.

The embodiment shown in FIG. 10 is similar to the one shown in FIG. 8 in that the layers of the layered structure are directed in the transversal direction of the article 1, i.e. the extension of the layered structure into the non-layered structure is carried out in the transversal direction. FIG. 11 shows a transversal sectional view of the embodiment shown in FIG. 10. FIG. 10 shows the article 1 when not in use, whereas FIG. 11 shows the article 1 in use, i.e. the shape provided by the stiffening element 6 when the article 1 is in use is shown in FIG. 11.

FIG. 10 clearly shows that the stiffening element 6 includes a piece of material formed into a layered structure. The layered structure is formed by folding a strip of the material. Because FIG. 10 shows a section taken in parallel with the folds of the folded strip of the material, the folds are not shown in FIG. 10. The material strip is provided with attachment means 25 (see FIGS. 12a-14b) for detachably attaching the layers to each other. This allows the folded, layered structure to be held together during use of the article 1. This also allows the layers to be detached from each other when the layered structure is to be unfolded to a non-layered structure. A portion of the attachment means 25 are also used to lock the article 1 in a rolled up or folded state after use (see FIG. 15).

The stiffening element 6 is fastened to the lower side 11 of the absorption member 5 using fastening means 35 (see also e.g. FIG. 12c) arranged in association with an upper side of the piece of material making up the layered structure, i.e. the part of the layered structure that faces the lower side 11 of the absorption member 5. Suitable fastening means for this purpose are adhesives and hook-and-loop materials. Which fastening means to use depends on what type of materials are used in the piece of material making up the layered structure and in the lower side 11 of the absorption member 5. As an example, adhesive may be suitable if the lower side 11 of the absorption member 5 is a plastic back sheet. As another example, hook material secured to, or forming part of, the layered structure may be suitable if the lower side 11 of the absorption member 5 has textile material properties.

The bond of the stiffening element 6 to the lower side 11 of the absorption member 5 may be permanent. At least, this bond should be significantly stronger than the bond between the layers in the layered structure to prevent the stiffening element 6 from coming loose when extending (unfolding) the layered structure.

FIG. 11 shows the same embodiment as shown in FIG. 10 but in a transversal, sectional view. Moreover, FIG. 11 shows the article 1 in use, which means that FIG. 11 shows the shape of the article 1 that is provided by the stiffening element during use of the article 1. As can be seen in FIGS. 10 and 11 the stiffening element 6 provides in this case a raised portion on the upper side of the absorbent member 5, i.e. of the article 1, which raised portion extends longitudinally over most of the crotch portion 3. Such a raised portion makes contact with the genitals of the wearer during use of the article and provides for better absorption of bodily fluids.

As shown in FIG. 11, the layered structure is folded such as to acquire the shape of a double-sided stairway (except for the outer layer close to the gripping flap 22) wherein the individual steps extend in the longitudinal direction of the article 1 and wherein the "top of the stairs" is located closest to the absorption member 5. The layered stiffening element 6 thereby acquires a triangular-like cross-section. An effect of this is, at least when using a flexible absorbent member 5, that the abovementioned raised portion is formed on the upper side of the absorbent member 5 during use of the article 1. A similar raised portion can be formed also without using a stairway-shaped stiffening element 6. The layered structure could for instance have a simple rectangular cross-section, but using some form of stairway-shaping in the design of the layered stiffening element 6 makes it possible to provide the stiffening element 6 with certain geometries. Not only "regular stairway shapes" are conceivable; by letting a certain layer be folded such as to overlap an adjacent layer various shapes can be arranged.

As shown in FIG. 11, the gripping flap 22 protrudes from the stiffening element 6 to make it easy for a user to get hold of it. Such a positioning of the gripping flap 22 is generally advantageous, irrespective of the embodiment. This detailed arrangement of the gripping flap 22 is not explicitly shown in the other figures of this document; in these other figures should the reference to the gripping flap 22 be interpreted more as an indication on where the flap 22 preferably should be positioned.

FIGS. 12-14 show examples of how a piece of material 60 can be formed into a layered structure and form a suitable stiffening element 6.

Figure 12A:
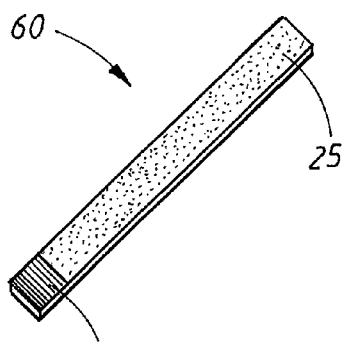
FIGS. 12a-12c show a first example of how a piece of material can be formed into a layered structure and form a suitable stiffening element according to embodiments of the invention.
Figure 12B:
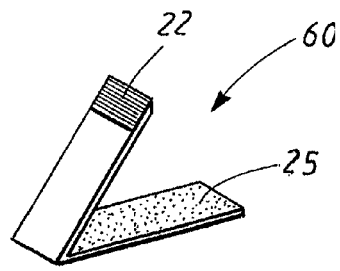

FIG. 12a shows a piece of material 60 that in this case is constituted of a strip of paper. This strip is provided with attachment means 25 in the form of an adhesive that allows detachment. The presence of adhesives is indicated with dots. The gripping flap 22 is free from adhesive. In FIG. 12b the material strip 60 has been partly folded and in FIG. 12c the piece of material 60 has been fully folded such as to form a layered structure suitable for use as a stiffening element 6. Due to the attachment means 25, the layers of the layered structure are detachably attached to each other.

Figure 12C:
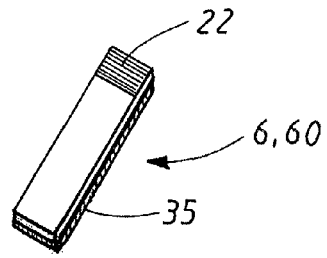

As indicated in FIG. 12c, the stiffening element 6 has been provided with fastening means 35 for fastening to the lower side 11 of the absorption member 5. The extension of the layered structure into a non-layered structure, i.e. the unfolding of the folded piece of material 60, is carried out by pulling the gripping flap 22. This can be visualized by studying FIGS. 12a-12c in the reverse order, i.e. by starting with FIG. 12c and ending up with FIG. 12a. The attachment means 25, in particular a portion close to the gripping flap 22, is useful also for locking a rolled up or folded used article 1, wherein the attachment means 25, as a particular example, is attached to the lower side 11 of the absorption member 5 (see FIG. 15).

FIGS. 13a-13c give an example of multiple folding of a similar piece of material 60 as shown in FIGS. 12a-12c. In principal, FIGS. 13a-13c correspond to FIGS. 12a-12c, respectively. FIG. 13a shows that the paper strip 60 is provided with folding indications 45. It is, of course, possible to fold the piece of material 60 many more times than shown in FIGS. 13a-13c. By increasing the number of folds it is possible to increase both size (height) and stiffness of the layered structure formed. How to fold depends, for instance, on the properties of the piece of material to be used and on what type of shape it is intended to provide the article 1 with.

FIGS. 14a-14b correspond to FIGS. 12a-12b and 13a-13b and show that the attachment means 25 is provided only onto a part of an individual layer. Thus, it is not necessary that the attachment means 25 is distributed over an entire side of the individual layer.

FIG. 15 shows, in a schematic view, a rolled up, used article 1', wherein the piece of material 60 has been extended (unfolded) and attached, by means of the attachment means 25, to the lower side 11 of the absorption member 5 such as to lock the article 1' in this rolled up mode.

Various materials are suitable for forming the piece of material 60 forming the layered structure. Besides paper, it is possible to use e.g. plastic films, hook material, foam or textile material. Further, the piece of material 60 may be a combination of integrated (e.g. lengthwise) or laminated materials, and flexible or not flexible. The stiffness of the material is not critical but may be important in the design since it determines how many times the material must be folded to acquire a stiffness sufficient for forming a suitable stiffening element 6.

Which attachment means 25 to use depends mainly on the properties of the material to be used for the layered structure. Some materials, such as certain plastic films, may even exhibit an inherent stickiness that can be used. The person skilled in the art, after having been provided with the information in this document, is capable of trying-out the detail of choosing a suitable attachment means 25 for the piece of material 60 to be used.

The stiffening element is sufficiently stiff for, as far as possible, preventing the absorbent article from being compressed or otherwise deformed in an uncontrolled manner during use of the article. As described above, the layered structure contributes significantly to the stiffness of the stiffening element 6. The more the layered structure contributes to the stiffness of the stiffening element 6, the less is the need for including other components or material in the article 1.

The stiffening element 6 should exhibit a stiffness that is higher than the material of the absorbent article 1 that surrounds the stiffening element. In relation to the embodiments described here, this means that the stiffening element 6 should be stiffer than the absorbent member 5. That the stiffness of the stiffening element 6 is higher than its surroundings has the effect that folding indications are provided along and/or around the stiffening element 6. These folding indications, together with e.g. the size and geometry of the stiffening element 6, determine which shape the article 1 will acquire during use.

In particular embodiments, the stiffening element 6 exhibits a stiffness in a dry state in the order of 1-15 N as measured according to ASTM D 4032-82.

The stiffening elements can have a variety of shapes and positions depending on the shape desired. Various advantageous shapes of absorbent articles are known to the person skilled in the art. In any case, the stiffening element(s) is/are arranged to, at least during use of the article, provide the article with a certain, predetermined shape that enhances the fit of the article to the wearer's body. A stiffening element may have a flat form before use but take a three-dimensional shape upon use of the article, i.e. when the article is affected by compressive forces generated by the thighs of the wearer. Alternatively, a stiffening element may have three-dimensional shape already before use of the article.

In particular embodiments, the stiffening element(s) is/are arranged such as to, at least during use of the article, provide the article with one or several of the following shapes:

A width at a transition between the crotch portion 3 and the front portion 2 that is less than the width at the front portion 2. This allows anchoring of the article to/between the thigh muscle tendons of the user and prevents the article from moving backwards during use. In particular embodiments, this width is in the range 15-45 mm.

A three-dimensional bowl-like shape in an area in the front portion 2 can enhance the body fit.

A ridge-shaped elevation that partially extends between the wearer's buttocks during use of the article can prevent rearward leakage.

A raised portion (hump) intended to make contact with the genitals of the wearer during use of the article can provide for better absorption of bodily fluids.

The embodiments shown in FIGS. 1 and 3 can be advantageous, because they have a simple structure and are relatively easy to manufacture.

The invention is not limited by the embodiments described above but can be modified in various ways within the scope of the claims. For instance, it is possible to include further components or parts into the stiffening element 6 in addition to the extendable layered structure. The disclosed article is multifunctional, i.e. that a significant part of the stiffening element 6, i.e. a part that significantly contributes to the stiffness of the stiffening element 6 and to the shape provided by this element, can be converted to a disposable means for locking a folded or rolled article after use. This means, for instance, that the stiffening element 6 may include a further component that partly contributes to the stiffness but does not take part in the locking function.

Moreover, the absorption member 5 may be structured in a different way; it may, for instance, include further components and/or layers.

The gripping flap 22 may be a separate item, such as a piece of a plastic material, that is attached to the piece of material 60 by means of the attachment means 25.

The stiffening element 6 may be provided with "hinges" in order to be more flexible in its longitudinal direction and thereby allow a better fit. Such "hinges" could be arranged in the form of longitudinally distributed slits or hook-free regions if the piece of material making up the layered structure includes a hook material.

The expression "rolled up or folded used article" should be interpreted in general terms as to cover partly rolled up, partly rolled, crimpled up and similar expressions and combinations thereof. It is clear that what is intended is any article configuration that provides for a convenient disposal after article has been used.

The invention claimed is:

1. An absorbent article having a longitudinal direction and a transverse direction, a front portion, a rear portion, a crotch portion located between the front portion and the rear portion, and a peripheral edge, said article comprising:
   an absorption member including an absorbent body for absorbing body fluids, said absorption member having an upper side intended to face a wearer during use of the article and a lower side intended to face away from the wearer during use of the article, and
   a stiffening element that, at least during use of the article, provides the article with a predetermined shape that enhances the fit of the article to the wearer's body,
   wherein the stiffening element is fastened to the lower side of the absorption member and comprises a piece of material formed into a layered structure that significantly contributes to the stiffness of the stiffening element, at least a part of the stiffening element having an elongated shape and extending in the longitudinal direction of the article, said part of the stiffening element being arranged to form a ridge on the upper side of the absorption member,
   wherein the layered structure can be extended to non-layered structure, and
   wherein the piece of material is provided with a first attachment for locking a rolled up or folded used article.

2. The absorbent article according to claim 1, wherein the layered structure is formed by folding the piece of material.

3. The absorbent article according to claim 1, wherein the piece of material comprises a second attachment for detachably attaching the layers in the layered structure.

4. The absorbent article according to claim 3, wherein a portion of the second attachment forms the first attachment.

5. The absorbent article according to claim 1, wherein said part of the stiffening element extends over at least a part of the rear portion of the article.

6. The absorbent article according to claim 1, wherein said ridge partially extends between the wearer's buttocks during use of the article.

7. The absorbent article according to claim 1, wherein said part of the stiffening element comprises a strip of material that has been folded to form said elongated shape.

8. The absorbent article according to claim 1, wherein the piece of material forming the layered structure is provided with a gripping flap arranged to allow extension of the layered structure when pulled.

9. The absorbent article according to claim 1, wherein the stiffening element exhibits a stiffness that is higher than a part of the absorbent article that surrounds the stiffening element.

10. The absorbent article according to claim 1, wherein the stiffening element is stiffer than the absorption member.

11. The absorbent article according to claim 1, wherein the absorption member comprises, at its upper side, a liquid-permeable top sheet and, at its lower side, a liquid-impermeable back sheet, wherein the absorbent body is arranged between said top sheet and said back sheet.

12. The absorbent article according to claim 1, wherein the stiffening element has a thickness that, at least during use of the article, displaces the absorption member to provide the article with the predetermined shape that enhances the fit of the article to the wearer's body.

\* \* \* \* \*